US007879558B2

(12) United States Patent
Kleinfeld

(10) Patent No.: US 7,879,558 B2
(45) Date of Patent: Feb. 1, 2011

(54) DIAGNOSTIC MARKERS FOR ISCHEMIA

(75) Inventor: Alan Kleinfeld, La Jolla, CA (US)

(73) Assignee: Torrey Pines Institute for Molecular Studies, San Diego, CA (US)

(*) Notice: Subject to any disclaimer, the term of this patent is extended or adjusted under 35 U.S.C. 154(b) by 479 days.

(21) Appl. No.: 11/841,480

(22) Filed: Aug. 20, 2007

(65) Prior Publication Data

US 2008/0004210 A1    Jan. 3, 2008

Related U.S. Application Data

(63) Continuation-in-part of application No. 10/243,566, filed on Sep. 13, 2002, now Pat. No. 7,262,017.

(60) Provisional application No. 60/322,523, filed on Sep. 14, 2001.

(51) Int. Cl.
*G01N 33/53* (2006.01)

(52) U.S. Cl. ......................................... 435/7.1; 436/815

(58) Field of Classification Search ....................... None
See application file for complete search history.

(56) References Cited

U.S. PATENT DOCUMENTS

| | | | |
|---|---|---|---|
| 4,071,413 | A | 1/1978 | Takahashi et al. |
| 4,369,250 | A | 1/1983 | Gindler |
| 4,491,631 | A | 1/1985 | Imamura et al. |
| 4,580,059 | A | 4/1986 | Wolfbeis et al. |
| 4,833,332 | A | 5/1989 | Robertson et al. |
| 5,225,329 | A | 7/1993 | Marks |
| 5,227,307 | A | 7/1993 | Bar-Or et al. |
| 5,449,607 | A | 9/1995 | Wilton |
| 5,470,714 | A | 11/1995 | Kleinfeld |
| 5,496,735 | A | 3/1996 | Schwertner |
| 5,512,429 | A | 4/1996 | Wilton |
| 5,604,105 | A | 2/1997 | Jackowski |
| 5,914,112 | A | 6/1999 | Bednar et al. |
| 5,977,174 | A | 11/1999 | Bradley et al. |
| 6,210,976 | B1 | 4/2001 | Sabbadini |
| 6,264,960 | B1 | 7/2001 | Robins et al. |
| 6,444,432 | B1 | 9/2002 | Kleinfeld |
| 6,461,875 | B1 | 10/2002 | Bar-Or et al. |
| 6,475,743 | B1 | 11/2002 | Bar-Or et al. |
| 6,492,179 | B1 | 12/2002 | Bar-Or et al. |
| 6,563,585 | B1 | 5/2003 | Rao et al. |
| 6,727,258 | B2 | 4/2004 | Baraldi |
| 6,750,030 | B2 | 6/2004 | Kleinfeld |
| 7,202,089 | B2 | 4/2007 | Kleinfeld |
| 2002/0168692 | A1 | 11/2002 | Cass et al. |
| 2002/0182197 | A1 | 12/2002 | Black et al. |
| 2004/0019109 | A1 | 1/2004 | Owman et al. |
| 2004/0077017 | A1 | 4/2004 | Karlstrom et al. |
| 2005/0239155 | A1 | 10/2005 | Alarcon et al. |
| 2005/0244864 | A1 | 11/2005 | Kleinfeld et al. |
| 2006/0257938 | A1 | 11/2006 | Kleinfeld et al. |

FOREIGN PATENT DOCUMENTS

| | | |
|---|---|---|
| EP | 1 043 587 | 6/2003 |
| SU | 1270706 | 9/1981 |
| WO | WO 91/09310 | 6/1991 |
| WO | WO 93/08276 | 4/1993 |
| WO | WO 94/06014 | 3/1994 |
| WO | WO 98/57171 | 11/1998 |
| WO | WO 98/57171 | 12/1998 |
| WO | WO 00/10014 | 2/2000 |
| WO | WO 00/20840 | 4/2000 |
| WO | WO 00/47734 | 8/2000 |
| WO | WO 00/74728 | 12/2000 |
| WO | WO 02/089656 | 11/2002 |
| WO | WO 03/093438 | 11/2003 |
| WO | WO 2005/093103 | 10/2005 |

OTHER PUBLICATIONS

Davies, et al. "Perioperative Variability of Binding of Lidocaine, Quinidine, and Propranolol After Cardiac Operations," *Journal of Thoracic and Cardiovascular Surgery*, vol. 96, No. 4, pp. 634-641, Oct. 1998.

Ford, et al. "Use of Serum Markers of Myocardial Injury for the Early Diagnosis of Acute Myocardial Infarction," *ACC Current Journal Review*, vol. 5, No. 3, pp. 86-89, May/Jun. 1996.

Kleinfeld, et al. "Increases in Serum Unbound Free Fatty Acid Levels Following Coronary Angioplasty," *American Journal of Cardiology*, vol. 78, No. 12, pp. 1350-1354, Dec. 15, 1996.

Glatz, et al. "Fatty-Acid-Binding Protein as a Plasma Marker for the Estimation of Myocardial Infarct Size in Humans," *BR Heart J*, vol. 71, pp. 135-140, 1994.

Patel, et al. "Serum Levels of Unbound Free Fatty Acids I: Normative Data in Term Newborn Infants," *Journal of American College of Nutrition*, vol. 16, No. 1, pp. 81-84, 1997.

Plesers, et al. "Fatty Acid-Binding Proteins as Plasma Markers of Tissue Injury," *Clinica Chimica Acta*, vol. 352, pp. 15-35, 2005.

Peuhkurinen, et al. "Changes in Myocardial Energy Metabolism in Elective Coronary Angioplasty," *Cardiovascular Research*, vol. 25, pp. 158-163, 1991.

Richieri, et al. "Equilibrium Constants for the Binding of Fatty Acids with Fatty Acid-Binding Proteins from Adipocyte, Intestine, Heart, and Liver Measured with the Fluorescent Probe ADIFAB," *The Journal of Biological Chemistry*, vol. 269, No. 39, pp. 23918-23930, Sep. 30, 1994.

Richieri, et al. "Thermodynamic and Kinetic Properties of Fatty Acid Interactions with Rat Liver Fatty Acid-Binding Protein," *The Journal of Biological Chemistry*, vol. 271, No. 49, pp. 31068-31074, Dec. 6, 1996.

(Continued)

*Primary Examiner*—Christopher L Chin
(74) *Attorney, Agent, or Firm*—Knobbe, Martens, Olson & Bear, LLP

(57) ABSTRACT

This invention relates to the diagnosis and monitoring of ischemia, including but not limited to myocardial and cerebral ischemia, by measuring the concentration of molecules that do not originate from the ischemic tissue but whose concentration in the blood and other fluids changes as a consequence of the ischemic state.

9 Claims, 8 Drawing Sheets

OTHER PUBLICATIONS

Richieri, et al. "Unbound Free Fatty Acid Levels in Human Serum," *Journal of Lipid Research*, vol. 36, No. 2, pp. 229-240, Feb. 1995.

Richieri, et al. "A Fluorescently Labeled Intestinal Fatty Acid Binding Protein. Interactions with Fatty Acids and its Use in Monitoring Free Fatty Acids," *The Journal of Biological Chemistry*, vol. 267, No. 33, pp. 23495-23501, Nov. 25, 1992.

Richieri, et al. "Kinetics of Fatty Acid Interactions with Fatty Acid Binding Proteins from Adipocyte, Heart, and Intestine," *The Journal of Biological Chemistry*, vol. 271, No. 19, pp. 11291-11300, May 10, 1996.

Ruben, et al. "Serum Levels of Unbound Free Fatty Acids II: The Effect of Intralipid Administration in Premature Infants," *Journal of the American College of Nutrition*, vol. 16, No. 1, pp. 85-87, 1997.

Samanta, et al. "Possible Physiological Role of Myocardial Fatty Acid Binding Protein in Phospholipid Biosynthesis," *Journal of Lipid Mediators*, vol. 1, pp. 243-255, 1989.

Samanta, et a. "Free Radical Scavenging by Myocardial Fatty Acid Binding Protein," *Free Radical Research Communications*, vol. 7, No. 2, pp. 73-82, 1989.

She, et al. "The Substrate Specificities of Four Different Lysophospholipases as Determined by a Novel Fluorescence Assay," *Biochem J.*, vol. 298, pp. 23-29, 1994.

Victor, et al. "Myocardial Tissue Free Fatty Acids," *Journal of Molecular and Cellular Cardiology*, vol. 16, No. 8, pp. 709-721, Aug. 1984.

*Textbook of Cardiovascular Medicine*, Eric J. Topol, Editor; Lippincott-Raven Publishers, Philadelphia, PA, 1998. Chapter 16, Harvey D. White, "Unstable Angina—Ischemic Syndromes." pp. 365-393.

Bansal, et al. "Stroke During Pregnancy and Puerperium in Young Females Below the Age of 40 Years as a Result of Cerebral Venous/Venous Sinus Thrombosis," *Japanese Heart Journal*, vol. 21, No. 2, pp. 171-183, Mar. 1980.

Agreeva, et al. "Structural and Functional Characteristics of Red Cell Membranes in Patients with Ischemic Stroke and Dyscirculatory Encephalopathy," *Zhurnal Nevrologii Psikhiatrii Imeni SS Korsakova*, vol. 94, No. 1, pp. 6-8, 1994.

Imre, et al., "Increased Proportion of Docosahexanoic Acid and High Lipid Peroxidation Capacity in Erythrocytes of Stroke Patients," *Stroke*, vol. 25, No. 12, pp. 2416-2420, 1994.

Brown, et al., "Fatty Acids and the Inhibition of Mitogen-Induced Lymphocyte Transformation by Leukemic Serum," *The Journal of Immunology*. vol. 131, No. 2, pp. 1011-1016, Aug. 1983.

Butko, et al. "Acidic Phospholipids Strikingly Potentiate Sterol Carrier Protein 2 Mediated Intermembrane Sterol Transfer," *Biochemistry*. vol. 29, pp. 4070-4077, 1990.

N. Bazán, et al. "Membrane Lipids in the Pathogenesis of Brain Edema: Phospholipids and Arachidonic Acid, the Earliest Membrane Components Changed at the Onset of Ischemia," *Advances in Neurology*, vol. 28: Brain Edema, Raven Press, New York, 1980, pp. 197-205.

N. Bazán, et al. "Effects of Ischemia and Electroconvulsive Shock on Free Fatty Acid Pool in the Brain," *Biochimica et Biophysica Acta*, 218, 1970, pp. 1-10.

M. Ikeda, et al. "Polyphosphoinositides as a Probably Source of Brain Free Fatty Acids Accumulated at the Onset of Ischemia," *Journal of Neurochemistry*, Raven Press, New York, 1986, pp. 123-132.

V. Kurien, "Serum-Free-Fatty-Acids After Acute Myocardial Infarction and Cerebral Vascular Occlusion," *The Lancet*, Jul. 16, 1966, pp. 122-127.

G. Richieri, et al., "Interactions of Long-Chain Fatty Acids and Albumin: Determination of Free Fatty Acid Levels Using the Fluorescent Probe ADIFAB," *Biochemistry*, vol. 32, 1993, pp. 7574-7580.

B. Weinberger, et al. "Effects of Perinatal Hypoxia on Serum Unbound Free Fatty Acids and Lung Inflammatory Mediators," *Biology of the Neonate*, vol. 79, 2001, pp. 61-66.

Li, et al. "High Throughput Screening Systems for Identification of Fatty Acid Uptake Inhibitors," *FASEB Journal*, vol. 20, No. 4, Part 1, Mar. 2006.

Richieri, et al. "Fatty Acid Binding Proteins from Different Tissues Show Distinct Patterns of Fatty Acid Interactions," *Biochemistry*, vol. 39, No. 24, 7197-7204, 2000.

Richieri, et al. "The Measurement of Free fatty Acid Concentration with the Fluorescent Probe ADIFAB: A Practical Guide for the Use of the ADIFAB Probe," *Molecular and Cellular Biochemistry*, vol. 192, pp. 87-94, 1999.

Kampf, et al. "Fatty Acid Transport in Adipocytes Monitored by Imaging Intracellular Free Fatty Acid Levels," *The Journal of Biological Chemistry*, vol. 279, No. 34, pp. 35775-35780, Aug. 20, 2004.

Ikeda, et al. "Polyphosphoinositides as a Probable Source of Brain Free Fatty Acids, Accumulated at the Onset of Ischemia," *Journal of Neurochemistry*, vol. 47, No. 1, pp. 123-132, 1986.

Banaszak, et al. "Lipid-Binding Proteins: A Family of Fatty Acid and Retinoid Transport Proteins," *Advances in Protein Chemistry*, vol. 45, pp. 90-151, 1994.

van Zoelen, et al. "An Exact General Analysis of Ligand Binding Displacement and Saturation Curves," *Biochemistry*, vol. 32, pp. 6275-6280, 1993.

Veerkamp, et al. "Structural and Functional Features of Different Types of Cytoplasmic Fatty Acid-Binding Proteins," *Biochimica et Biophysica Acta*, vol. 1081, pp. 1-24, 1991.

Kohashi, et al. "Fluorescence Reaction of Bilirubin with Zinc Ion in Dimethyl Sulfoxide and Its Application to Assay of Total Bilirubin in Serum," *Analytica Chimica Acta*, vol. 365, Nos. 1-3, pp. 177-182, Jun. 5, 1998.

Sacchettini, et al. "The Structure of Crystalline *Escherichia coli*-Derived Rat Intestinal Fatty Acid-Binding Protein at 2.5-Å Resolution," *The Journal of Biological Chemistry*, Vo. 263, No. 12, pp. 5815-5819, Apr. 25, 1988.

Evans, et al. "The Chemical Modification of Cysteine-69 of Rat Liver Fatty Acid-Binding Protein (FABP): A Fluorescence Approach to FABP Structure and Function," *Molecular and Cellular Biochemistry*, vol. 98, Nos. 1-2, pp. 135-140, Oct. 1990.

Lowe, et al. "Expression of Rat Intestinal Fatty Acid-Binding Protein in *Escherichia coli*," *The Journal of Biological Chemistry*, vol. 262, No. 12, pp. 5931-5937, Apr. 25, 1987.

DIAGNOSTIC MARKERS FOR ISCHEMIA

RELATED APPLICATIONS

This application is a continuation-in-part of U.S. application Ser. No. 10/243,566, filed Sep. 13, 2002 which claims priority to U.S. Provisional Application No. 60/322,523, filed Sep. 14, 2001, which are incorporated herein by reference.

BACKGROUND OF THE INVENTION

1. Field of the Invention

This invention relates to the diagnosis and monitoring of ischemia, including but not limited to myocardial and cerebral ischemia, by measuring the concentration of molecules that do not originate from the ischemic tissue but whose concentration in the blood and other fluids changes as a consequence of the ischemic state.

2. Description of the Related Art

Ischemia is a reduction in blood flow. This reduction may occur for a variety of reasons, including but not limited to thrombosis, embolism, aneurysm, spasm, or collapse of a blood vessel due to deterioration. Because of the reduction in blood flow the tissue that would otherwise be nourished may no longer receive sufficient nutrition to maintain cellular integrity, it also may not be able to remove sufficient amounts of cellular waste products and it may also result in inadequate exchange of blood gases such as oxygen and carbon dioxide. The inability to transfer sufficient oxygen to the cells (hypoxia) may have many of the same consequences of ischemia and can also be detected by the same methods claimed in this invention.

If ischemia persists for a sufficient time, that is, if oxygenated blood flow is not restored, then the cells of the tissue normally perfused by the blood flow, will begin to die. This may occur gradually over time and may be unnoticed until sufficient cell destruction has occurred so that the function of the organism is significantly impaired. An example may be the gradual deterioration of circulation to the extremities or other body parts that occurs in diabetes. The disruption of blood flow may also occur more acutely. This includes but is not limited to thrombus formation that results in reduction of blood flow through the coronary arteries, lodging of an embolism in a cerebral ischemia and similar events in the kidney and limbs.

For either a gradual or an acute time course, the earlier the ischemic/hypoxic condition can be detected and the sooner palliative therapy can be applied, the better will be the outcome for tissue and organism. For example, early detection of the diabetic-mediated ischemia in extremities might avoid amputation and early detection and relief of acute blockages to the heart or brain significantly reduces mortality and morbidity.

Unfortunately, early detection of ischemia/hypoxia is often not possible. For example, the ECG which is the primary early diagnostic tool for acute coronary syndromes is less than 40% sensitive. For stroke patients the only tools available are either a CT scan or MRI, both of which can only determine if the patient has a hemorrhage in the first several hours after symptoms began. Only much later, when it is too late to administer the only treatment of ischemic stroke, thrombolytic therapy, are these imaging methods able to determine if an ischemic stroke has occurred. Thrombolytic therapy must be administered within 3 hours of symptoms. For other organs there are no well established methods for early detection of ischemia. Thus a sensitive, accurate and rapid test for ischemia is needed for the diagnosis and treatment of patients.

In the final stages of ischemia, when cells begin to die (necrosis), they may release some of their contents into the blood. These are primarily intracellular proteins that are released because the normal barrier to containment, the cell's membrane, is compromised by biochemical changes associated with death. Often these molecules are tissue specific, for example, cardiac troponin in the case of the heart. Although these molecules accurately reflect the presence of disease, they generally require several hours after symptoms occur to reach levels of significance in blood and they are only released from dead or dying cells. Thus in addition to sensitivity and accuracy an important feature of a test for ischemia would be its ability to detect the ischemic state well before necrosis.

In addition to the release of molecules from the ischemic tissue that are markers of necrosis, the ischemic event may generate a series of biochemical changes that can result in the change in concentration of molecules within the blood or other fluids that do not originate from the ischemic tissue. These are referred to in this invention as ischemic markers. The generation of ischemic markers can occur, for example, when the ischemic tissue generates molecules that are then converted to different molecules by a non-ischemic tissue or the ischemic tissue generates molecules that activate, from non-ischemic tissue, the release of different molecules into body fluids. Examples of this are the generation of norepinephrine, $TNF_\alpha$ and natriuretic peptides by ischemic cardiac or cerebral tissue. The norepinephrine, $TNF_\alpha$ and natriuretic peptides so generated activate lipolysis in adipose tissue resulting in the elevation of free fatty acids in blood. In another example, sphingosine released from the ischemic myocardium is converted to sphingosine-1-phosphate in platelets and may then be detected in blood (Yatomi, et al. (1997) Journ. Biol. Chem. vol. 272: pages 5291-5297; U.S. Pat. No. 6,210,976).

In addition to diagnosing the presence of disease, levels of ischemic markers may predict risk of future deleterious events. Numerous in vitro studies reveal that elevated free fatty acids (FFA) are potent perturbants of many cellular functions, and clinical evidence for a direct role of FFA is strongly suggested by a number of studies pointing to their potential role in cardiovascular disease (Leaf A. Circulation 104: 744-745, 2001; Oliver M F and Opie L H. The Lancet 343: 155-158, 1994; Paolisso G, et al. American Journal of Cardiology 80: 932-937, 1997; Carlsson M, et al. Arterioscler throm Vasc Biol 20: 1588-1594, 2000). Elevations in total plasma FFA are associated with increased risks of cardiac arrhythmias (Kurien V A and Oliver M F. Br Heart J 32: 556, 1970; Kurien V A and Oliver M F. The Lancet April 18: 813-815, 1970; Leaf A. Circulation 104: 744-745, 2001; Oliver M F. Am J Med 112: 305-311, 2002) and death in non-acute cardiovascular disease (Jouven X, et al. Circulation 104: 756-761, 2001; Pilz S, et al. J Clin Endocrinol Metab 91: 2542-2547, 2006) and therefore are a particularly unwelcome consequence of acute coronary syndrome (ACS).

Moreover, these molecules, at sufficient levels, may themselves mediate cellular effects that result in deleterious outcomes. For example, a large long term study of apparently healthy men revealed that increasing levels of total serum free fatty acids (FFA), although within the normal range, were associated with an increased risk of sudden death 22 years later. It was speculated that this increased rate of death was a consequence of FFA induced cardiac arrhythmias. In another example, use of the combination of glucose-insulin-potassium (GIK) in patients suffering from acute myocardial infarcts, produced a significant reduction in mortality relative to patients who did not receive GIK. One theory for this beneficial effect is the reduction in serum total FFA produced by GIK. Thus there is a need to be able to monitor ischemic markers to evaluate longer term risk of disease and to help to decide on the type of therapeutic intervention to reduce the increased risk associated with what may be a chronic ischemic state.

SUMMARY OF THE INVENTION

The present invention describes the use in the diagnosis and monitoring of ischemia, of measuring the concentration in blood and/or other fluids of molecules that do not originate from the ischemic tissue. These molecules are called ischemic markers. The change in the concentration of these ischemic markers, relative to the non-ischemic condition, is indicative of some type of ischemia.

In one embodiment, the present invention is drawn to a method of detecting a condition which is indicative of ischemia in a mammal which includes the steps of:
 (a) measuring a level of an ischemic marker in a test sample from a fluid of the mammal; and
 (b) determining if the level of the ischemic marker measured in the test sample correlates with ischemia in the mammal. In a preferred embodiment, the mammal is a human. The fluid used for the test sample may be selected from the group including but not limited to blood, serum, plasma, saliva, bile, gastric juices, cerebral spinal fluid, lymph, interstitial fluid or urine. In a preferred embodiment, the fluid used for the test sample is blood.

In one embodiment, the ischemic marker is a lipid. The lipid may be selected from the group including, but not limited to, a sphingolipid, a lysolipid, a glycolipid, a steroid, and an eicosanoid, including leukotrienes, prostacyclins, prostaglandins and thromboxanes. In one embodiment, the sphingolipid used as the ischemic marker may be sphingosine, or a metabolite thereof including ceramide (Cer, N-acylsphingosine), sphingosine-1-phosphate, sphingosylphosphorylcholine, or dihydrosphingosine, for example. In a more preferred embodiment, the lipid is a fatty acid.

The disclosed method may be used for detection of ischemia in any organ or tissue including but not limited to the heart, brain, kidney or a limb.

In one embodiment of the invention, a component of the ischemic marker which is soluble in an aqueous buffer is detected. In an alternate embodiment, the component of the ischemic marker which is not soluble in an aqueous buffer is detected.

The ischemic marker may be detected by spectroscopic means including but not limited to UV/VIS, infrared, microwave, radio, absorption or emission spectroscopes. Chromatographic procedures are also encompassed by the present invention, including but not limited to HPLC, low pressure chromatography, medium pressure chromatography, and gas chromatography. Detection of the ischemic marker by electron spin resonance using a spin label is also encompassed by the invention. In an alternate embodiment, the ischemic marker may be detected by an antibody or receptor molecule, immunoassay or enzymatic assay.

In a preferred embodiment, the method may include an initial step of selecting a mammal presenting symptoms of ischemia. In some embodiments, the method may also include the step of administering anti-ischemic therapy if the level of ischemic marker correlates with ischemia in said mammal. The anti-ischemic therapy may include a means to lower levels of serum fatty acids. In some embodiments, the anti-ischemic therapy is reperfusion therapy, antithrombolytic therapy, angiogenic therapy or surgery.

In some embodiments, the determination step is a comparison between said measured level of said ischemic marker and a predetermined value for the level of said marker. In some embodiments, the predetermined value for the level of the marker is indicative of the non-ischemic condition.

In one embodiment, the ischemic marker is an unbound or water-soluble free fatty acid. In a preferred embodiment, the unbound or water-soluble free fatty acid is detected by a protein that binds fatty acid. In a preferred embodiment, the protein that binds an unbound or water-soluble free fatty acid is fluorescent and exhibits a fluorescence that is different when the fatty acid is bound than when it is not bound. In some embodiments, the protein is one of the family of intracellular Fatty Acid Binding Proteins (FABPs) that have molecular weights between about 13,000 and 16,000 Dalton. In a preferred embodiment, the FABP is a rat intestinal FABP. In a preferred embodiment, the FABP is covalently labeled with acrylodan at position 27. In a more preferred embodiment, the acrylodan-labeled FABP is the leucine 72 to alanine mutant.

In some embodiments, a level of the unbound or water-soluble free fatty acid greater than 2 standard deviation units above an average value of a level of the unbound or water-soluble free fatty acid determined from a non-ischemic population is indicative of the ischemic condition. In some embodiments, a level of the unbound or water-soluble free fatty acid greater than about twice an average value of a level of the unbound or water-soluble free fatty acid determined from a non-ischemic population is indicative of the ischemic condition. In some embodiments, a level of the unbound or water-soluble free fatty acid greater than about 5 nM is indicative of the ischemic condition.

In an alternate embodiment, the protein that binds an unbound or water-soluble free fatty acid is albumin. In a preferred embodiment, the albumin is covalently labeled with 7-hydroxycoumarin or anthraniloyl.

In an alternate embodiment, the ischemic marker is total free fatty acid. In an alternate preferred embodiment a level of the total free fatty acid greater than 2 standard deviation units above an average value for the level of the total free fatty acid determined from a non-ischemic population is indicative of the ischemic condition. In an alternate preferred embodiment, a level of the total free fatty acid greater than about twice an average value of a level of the total free fatty acid determined from a non-ischemic population is indicative of the ischemic condition. In another embodiment, the ischemic marker is a ratio of total free fatty acid to albumin.

In some embodiments, the ratio of total free fatty acid to albumin greater than about two standard deviation units above an average value of the ratio of total free fatty acid to albumin determined from a non-ischemic population is indicative of the ischemic condition. In some embodiments, the ratio of total free fatty acid to albumin greater than about twice an average value of the ratio of total free fatty acid to albumin determined from a non-ischemic population is indicative of the ischemic condition.

In one embodiment, a method of determining response in a mammalian patient to a treatment for ischemia is described which includes the steps of detecting ischemia as described above and determining if the level of the ischemic marker is trending towards the level of the marker in the non-ischemic condition. In preferred embodiments, the pre-determined value for the marker is indicative of a non-ischemic condition.

In preferred embodiments, the ischemic marker is an unbound free fatty acid, total free fatty acid or a ratio of total free fatty acid to albumin. In preferred embodiments, the treatment for ischemia is selected from reperfusion therapy, antithrombolytic therapy, angiogenic therapy, surgery and combinations thereof. Preferably, the treatment is reperfusion therapy which includes but is not limited to angioplasty or administration of a thrombolytic agent.

In preferred embodiments, at least one measurement of the level of the ischemic marker is taken 30 minutes to 5 hours after the treatment for ischemia. In preferred embodiments, the mammalian patient is human.

In preferred embodiments, the fluid is blood, serum, plasma, saliva, bile, gastric juices, cerebral spinal fluid, lymph, interstitial fluid or urine.

In some preferred embodiments, the ischemic marker is a sphingolipid, a lysolipid, a glycolipid, a steroid or an eicosanoid. In some preferred embodiments, the ischemic marker is sphingosine, ceramide, sphingosine-1-phosphate, sphingosylphosphorylcholine, or dihydrosphingosine.

In one embodiment, a method of identifying patients at high risk for hemorrhage after receiving reperfusion therapy is described which includes the steps of:

measuring the level of an ischemic marker in a body fluid sample from the patient before reperfusion therapy;

comparing the measured level of the ischemic marker from the patient to a threshold level of an ischemic marker, where the threshold level is determined from measuring the ischemic marker in body fluid of an ischemic population;

determining a ratio of the measured level of the ischemic marker from the patient to the threshold level; and correlating the ratio with the relative risk for hemorrhage after reperfusion therapy such that a high ratio indicates a high risk. In a preferred embodiment, the ischemic marker is selected from the group including unbound free fatty acid, total free fatty acid and a ratio of total free fatty acid to albumin.

Preferred embodiments are directed to a method of treating patients at high risk for hemorrhage after receiving reperfusion therapy by identifying a patient at high risk for hemorrhage after reperfusion therapy using the method described above and treating the high-risk patient with a therapy to reduce levels of unbound free fatty acid, total free fatty acid or the ratio of total free fatty acid to albumin. Preferably, the therapy includes but is not limited to administration of acipimox, glucose-insulin-potassium compositions and albumin compositions.

In one embodiment, a method of identifying patients at high risk for mortality within three years after an ischemic event is described which includes the steps of:

measuring the level of an ischemic marker in a body fluid sample from the patient before treatment with an anti-ischemic therapy;

comparing the measured level of the ischemic marker from the patient to a threshold level of the ischemic marker, where the threshold level is determined from measuring the ischemic marker in body fluid of an ischemic population;

determining a ratio of the measured level of the ischemic marker from the patient to the threshold level; and correlating the ratio with the relative risk for mortality within three years after an ischemic event such that a high ratio indicates a high risk. In a preferred embodiment, the ischemic marker is selected from the group including unbound free fatty acid, total free fatty acid and a ratio of total free fatty acid to albumin.

Embodiments of the invention are directed to a method of treating patients at high risk for mortality within three years after an ischemic event by identifying a patient at high risk for mortality within three years after an ischemic event using the method described above and treating the high-risk patient with a therapy to reduce the levels of unbound free fatty acid, total free fatty acid or the ratio of total free fatty acid to albumin. Preferably, the therapy includes but is not limited to administration of acipimox, glucose-insulin-potassium compositions and albumin compositions. Mortality may be caused by myocardial infarction or arrhythmias.

In one embodiment, a method of identifying patients at high risk for hemorrhage is described which includes the steps of:

measuring a lipid component in a body fluid sample from the patient;

comparing the measured level of the lipid component from the patient to a threshold level of a lipid component, wherein the threshold level is determined from measuring a lipid component in body fluid of a normal population that does not have ischemia;

determining a ratio of the measured level of the lipid component from the patient to the threshold level; and correlating the ratio with the relative risk for hemorrhage such that a high ratio indicates a high risk. In a preferred embodiment, the lipid component is selected from the group including unbound free fatty acid, total free fatty acid and a ratio of total free fatty acid to albumin.

In another embodiment, a method of treating patients at high risk for hemorrhage is described which includes the steps of:

identifying a patient at high risk for hemorrhage using the method described above; and treating the high-risk patient with an anti-ischemic therapy. In one embodiment, the anti-ischemic therapy is selected from the group including but not limited to acipimox, glucose-insulin-potassium compositions and albumin compositions.

In one embodiment, a method of assessing long-term risk in non-acute patients is described which includes the steps of:

measuring the level of an ischemic marker in a body fluid sample from the patient before treatment with an anti-ischemic therapy;

comparing the measured level of the ischemic marker from the patient to a threshold level of the ischemic marker, where the threshold level is determined from measuring the ischemic marker in body fluid of an ischemic population;

determining a ratio of the measured level of the ischemic marker from the patient to the threshold level; and correlating the ratio with the relative risk for mortality such that a high ratio indicates a high risk. In a preferred embodiment, the ischemic marker is selected from the group including unbound free fatty acid and a ratio of total free fatty acid to albumin.

In preferred embodiments, the therapy is monitored by measuring the level of the ischemic marker in a body fluid sample from the patient after the anti-ischemic therapy; and determining if the level of the ischemic marker is trending towards a pre-determined value. In preferred embodiments, the predetermined value for the level of the marker is indicative of a non-ischemic condition. Preferably, at least one measurement of the level of the ischemic marker in the body fluid is taken 30 minutes to 5 hours after the treatment.

In more preferred embodiments of the methods described above, the ischemic marker is unbound free fatty acid and a level of unbound free fatty acid of 1.5 to 2.5 nM signifies low risk, a level of unbound free fatty acid of 2.5 to 4.0 nM signifies low to medium risk, a level of 4.0 to 7.5 nM unbound free fatty acid signifies medium to high risk and a level of unbound free fatty acid greater than 7.5 nM signifies highest risk. Preferably, the level of unbound free fatty acid is determined in plasma or serum. More preferably, the level of unbound free fatty acid is determined by binding to acrylodan-labeled intestinal fatty acid binding protein with a substitution of Ala for Leu at position 72 (ADIFAB2). In such preferred embodiments, the binding is carried out at a temperature of 20-24° C.

Further aspects, features and advantages of this invention will become apparent from the detailed description of the preferred embodiments which follow.

BRIEF DESCRIPTION OF THE DRAWINGS

These and other feature of this invention will now be described with reference to the drawings of preferred embodiments which are intended to illustrate and not to limit the invention.

DETAILED DESCRIPTION OF THE PREFERRED EMBODIMENT

Figure 1:
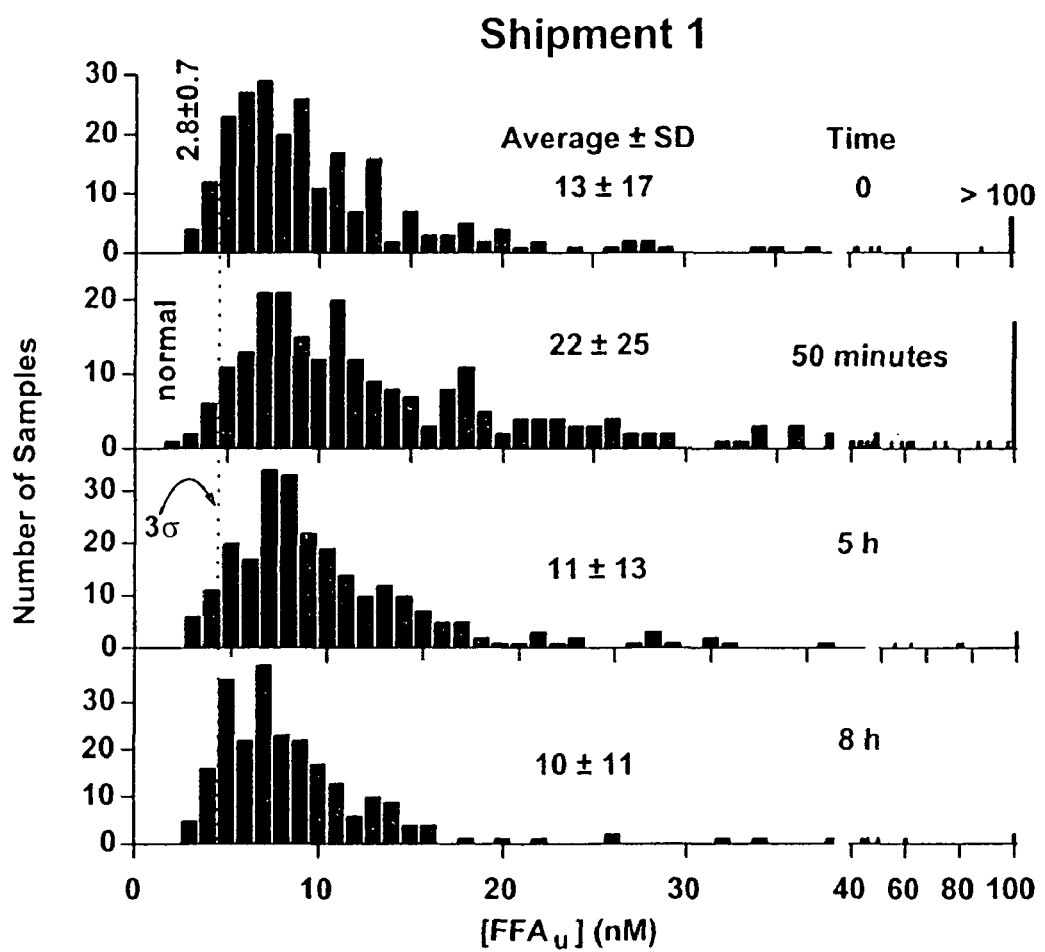
FIG. 1 shows the level of unbound free fatty acid in blood samples taken from the Thrombolysis in Myocardial Infarction II (TIMI II) study of patients with AMI. Patients included in the study presented to the Emergency Department within 4 hours of onset of symptoms. Histogram representation shows the results of [$FFA_u$] measurements in blood draws at times 0 (time of admission into Emergency Dept.), 50 min., 5 hour and 8 hour for each of the first 250 patients, measured with ADIFAB2. Note that "[$FFA_u$]" refers to the concentration of unbound free fatty acid.

While the described embodiment represents the preferred embodiment of the present invention, it is to be understood that modifications will occur to those skilled in the art without departing from the spirit of the invention. The scope of the invention is therefore to be determined solely by the appended claims.

The present invention describes the use, in the diagnosis and monitoring of ischemia, of measuring the concentration of molecules that do not originate from the ischemic tissue in blood and/or other fluids. These molecules are called ischemic markers. The change in the concentration of these ischemic markers, relative to the non-ischemic condition, is indicative of some type of ischemia. A marker is considered not to originate from the ischemic tissue even though some fraction may have so originated, so long as that fraction represents only a small portion of the marker present in the sample, e.g., 20%, 10%, 5%, 2%, 1% or less.

In one embodiment, the ischemic marker is a lipid component such as a fatty acid. Total fatty acids may be determined by methods well known in the art such as taught in U.S. Pat. No. 4,071,413, U.S. Pat. No. 5,512,429, U.S. Pat. No. 5,449,607, and U.S. Pat. No. 4,369,250 all of which are incorporated herein by reference. Levels of total fatty acid obtained by these methods may be compared with levels obtained from normal individuals in order to detect an ischemic condition in an individual. In a preferred embodiment, a ratio of total fatty acid to albumin is determined and compared with a normal population.

In another embodiment, unbound free fatty acid levels are measured in a bodily fluid as described below. Unbound free fatty acids ($FFA_u$) are the portion of free fatty acids soluble in the aqueous phase. In most body fluids free fatty acid (FFA) is mostly bound to proteins, for example, albumin, and membranes but a significant minority is unbound ($FFA_u$) and soluble in the aqueous phase. $FFA_u$ are also referred to as water-soluble free fatty acids.

The bodily fluid may be selected from the group including cerebral spinal fluid, blood, serum, plasma, urine, saliva, lymph, gastric juices, interstitial fluid or bile In preferred embodiments, the fluid used for the test sample is taken from blood.

In one embodiment, any assay that provides an indication of the level of unbound free fatty acid ($FFA_u$) in body fluid relative to an asymptomatic population may be used in the diagnostic method to detect an ischemic condition. Preferably a threshold value is determined from a normal population that does not have an ischemic condition. In one embodiment, the threshold value is a concentration of $FFA_u$ in a body fluid that is significantly higher than the concentration of $FFA_u$ in the body fluid of a control population that does not have an ischemic condition. In one embodiment, the threshold value is a concentration of $FFA_u$ in a body fluid that is at least about two standard deviations greater than an average concentration of $FFA_u$ in a body fluid of a control population that does not have an ischemic condition. In another embodiment, the threshold concentration of $FFA_u$ in a body fluid is at least about 5 nM. In another embodiment, the threshold concentration of $FFA_u$ in a body fluid is at least about twice the average concentration of $FFA_u$ in a body fluid of a control population that does not have an ischemic condition.

The present methods are particularly valuable when applied to selected patient populations. Thus, in one embodiment, the method is applied to a sample from an individual at risk for ischemia, such as diabetic patients, or surgery patients, or patients with familial or lifestyle risk factors. In another embodiment, the method is applied to a patient presenting symptomology consistent with ischemia or an ischemic event, or a patient suspected of having ischemia. Particular patient subpopulations that can be selected include patients having symptomology consistent with cardiac ischemia, brain ischemia, kidney ischemia, limb ischemia, or other clinically-significant ischemia. The method may be selectively applied to patients presenting symptomology consistent with or inconsistent with one particular type of ischemia. Non-limiting examples would be selection of a patient having ischemic symptoms other than cardiac ischemia, or symptoms other than brain ischemia, or symptoms other than peripheral or diabetic-related ischemia. The present method may similarly be used to detect ischemia in cardiac patients in the absence of myocardial infarction by selecting an appropriate patient population. In one embodiment of any of the methods of the present invention, the patient is a mammal, and in a particular embodiment, the patient is a human.

In still a further embodiment of the invention, the method of the present invention further includes a treatment step. Thus, a patient is first tested for an ischemic condition, represented by elevation of one of the markers discussed herein. Patients having elevated levels of the marker are then treated with anti-ischemic therapy of any suitable type, such as reperfusion therapy, antithrombolytic therapy, angiogenic therapy, surgery, or the like. For example, patients may advantageously be tested within 10, 7, 5, or 3 hours of an ischemic event or symptom, and may then receive anti-ischemic therapy within 3, 2, or preferably 1 hour of the test.

In one embodiment, the present invention uses a fluorescently-labeled fatty acid binding protein (FABP) to measure an increased amount of unbound free fatty acid ($FFA_u$) in body fluid samples associated with an ischemic condition by quantitatively detecting a shift in fluorescence associated with binding of a $FFA_u$ molecule to the fluorescently-labeled FABP. In serum, free fatty acid (FFA) is mostly bound to albumin but a significant minority is unbound ($FFA_u$) and soluble in the aqueous phase. This invention utilizes the method substantially as described in U.S. Pat. No. 5,470,714, which is incorporated herein by reference. A variety of FABP and fluorescent labels can be used in detecting levels of $FFA_u$ in body fluids such as blood. These include, but are not limited to, rat intestinal FABP (I-FABP), human adipocyte FABP (A-FABP) and rat heart FABP (H-FABP). Site-specific mutant forms of these FABP, in which one or more amino acid residues have been altered (inserted, deleted and/or substituted) are also useful in the method and include, for example, substitutions of Cys in I-FABP at positions 27, 81, 82, 84, an Ala substitution at residue 72 of I-FABP, and a Lys substitution at residue 27 of H-FABP. The FABP molecules may be fluorescently-labeled using a variety of known labels including but not limited to acrylodan, danzyl aziridine, 4-[N-[(2-iodoacetoxy)ethyl]-N-methylamino]-7-nitrobenz-2-oxa-1, 3-diazole ester (IANBDE), and 4-[N-[(2-iodoacetoxy)ethyl]-N-methylamino-7-nitrobenz-2-oxa-1,3-diazole (IANBDA). Any label may be used in the practice of the invention as long as a measurable difference may be detected upon binding of a free fatty acid. For example, a difference in wavelength, signal intensity, or polarization, or lifetime may be monitored. Further examples of labels which may be used include, but are not limited to, chromophores which produce a change in absorbance or optical activity and spin labels which change is detectable by electron spin resonance. In a preferred embodiment, a fluorescently-labeled FABP is acrylodan-derived recombinant rat intestinal fatty acid binding protein (referred to as ADIFAB). Derivatization with acrylodan was performed using known methods substantially as previously described (U.S. Pat. No. 5,470,714 & Richieri, G. V, et al., J. Biol. Chem., (1992) 276: 23495-23501), and ADIFAB is commercially available (FFA Sciences LLC, San Diego, Calif.). Concentrations of $FFA_u$ can be determined by the binding of the $FFA_u$ to the fluorescently labeled fatty acid binding protein (FABP). A different fluorescence is exhibited when no FFA is bound to the fluorescently-labeled FABP. The concentration of $FFA_u$ can be determined from the fluorescence difference. The wavelength emitted by the fluorescently-labeled FABP depends upon the label and protein used. In one embodiment, the protein is either I-FABP or a I-FABP with a substitution of Ala for Leu at position 72 where the label is acryolodan. These species are referred to as ADIFAB and ADIFAB2, respectively.

Briefly, ADIFAB2 was obtained as follows. First, a restriction fragment, carrying the $Ala^{72}$ mutation and appropriate complementary ends, was substituted for the wild-type restriction fragment spanning the SalI site at position 211 in the I-FABP cDNA sequence (Alpers, et al. (1984) Proc. Natl. Acad. Sci U.S.A. 81: 313-317) and a PmeI site at position 291, which was introduced by site-specific mutagenesis. The mutated restriction fragment was constructed by annealing partially complementary synthetic oligonucleotides carrying the desired sequence, "filling in" single-stranded regions with the DNA polymerase Klenow fragment, and digesting with SalI and PmeI to give the appropriate termini. The $Ala^{72}$ substituted I-FABP cDNA was inserted into the pET11 vector and was expressed in the BL21(DE3) strain. The mutant I-FABP was purified essentially by the method of Lowe, et al. (Lowe, et al. (1987) J. Biol. Chem. 262: pages 5931-5937) and yielded about 100 mg of purified protein per liter of *Escherichia coli* culture. Acrylodan derivatization was done as described previously for ADIFAB (see U.S. Pat. No. 5,470, 714, incorporated herein by reference). Lipidex-5000 chromatography was used to remove free acrylodan.

The binding affinities of ADIFAB2 have been found to be about 10-fold greater than ADIFAB. The wavelength emitted by these fluorescently-labeled FABP's is about 420 to 470 nm. The emission wavelength for the FFA bound to the fluorescently-labeled FABP is about 495 to 580 nm. It will be understood that those skilled in the art can readily substitute other fluorescently-labeled FABP in the disclosed assay.

The assay for determination of $FFA_u$ levels in aqueous samples measures the intensity of a shift in fluorescence from a first wavelength, at which the derivatized FABP fluoresces when no FFA is bound, to a second wavelength, at which the derivatized FABP fluoresces when a molecule of FFA is bound, and the concentration of $FFA_u$ is then determined from the ratio ("R" value) of the two intensities of fluorescence wavelengths as described in U.S. Pat. No. 5,470,714 and Richieri, et al. (1995) J. Lipid Research, vol. 36: pages 229-

240, both of which are incorporated herein by reference. Briefly, the ratio is calculated using the following formula:

$$R = \frac{I(1) - I(1)\text{blank}}{I(2) - I(2)\text{blank}}$$

wherein, I(1) and I(1) blank are the measured fluorescence intensities for a sample containing ADIFAB or ADIFAB2 and a blank sample containing all reagents except ADIFAB or ADIFAB2, respectively at wavelength "1"; and I(2) and I(2) blank are the corresponding fluorescence intensities at wavelength "2". For ADIFAB, wavelength "1" is in preferably (but not absolutely) in the range of 495 and 515 nm and wavelength "2" is in the range from 422 to 442 nm. Measurements of fluorescence intensities may be obtained using standard techniques. As recognized by those skilled in the art, under appropriate conditions, the Iblank intensities in the above equation can be neglected.

Quantitative detection of levels of body fluid $FFA_u$ that are elevated over body fluid $FFA_u$ levels found in normal healthy individuals can be used to diagnose an ischemic condition. In one embodiment, an ischemic condition is indicated by a concentration of unbound or water-soluble free fatty acid in a body fluid sample that is significantly higher than the concentration of unbound or water-soluble free fatty acid in a body fluid sample of a control population that does not have an ischemic condition. In one embodiment, an ischemic condition is detected by levels of unbound or water-soluble free fatty acid in a body fluid sample that exceed the average normal levels of unbound or water-soluble free fatty acid in a body fluid sample by about 2 standard deviations. In another embodiment, unbound or water-soluble free fatty acid levels which are greater than about 5 nM are indicative of an ischemic condition. In another embodiment, a level of unbound or water-soluble free fatty acid in a body fluid sample greater than about twice the average value of unbound or water-soluble free fatty acid determined from a body fluid sample from a non-ischemic population is indicative of the ischemic condition. Elevated levels of unbound or water-soluble free fatty acid in a body fluid sample which are considerably higher may also be detected.

The diagnostic method of the present invention is based on the discovery that patients experiencing an ischemic condition have elevated levels of lipids such as $FFA_u$ in body fluids such as blood, compared to normal levels of body fluid $FFA_u$ in healthy individuals. While the diagnostic method may be carried out at any time, preferably, the test is carried out within 24 hours of the ischemic event. More preferably, the test is carried out within 10 hours of the ischemic event. Most preferably, the test is carried out within 3 hours of the ischemic event so that treatment may be initiated. Many treatments for ischemic conditions such as cardiac ischemia must be initiated quickly (within hours) in order to be effective. Treatment without a correct diagnosis can be most deleterious to the patient. The ability to quickly diagnose an ischemic condition is an advantage of the invention described here.

Briefly, the $FFA_u$ assay and determinations were performed as follows. Blood samples were diluted 100-fold in buffer (20 mM N-2-hydroxyethyl-piperazine-N'-2-ethane sulfonic acid (HEPES), 150 mM NaCl, 5 mM KCl and 1 mM $Na_2HPO_4$, adjusted to pH 7.4), yielding a serum albumin concentration of about 6 µM. A solution of fatty acid-free albumin plus ADIFAB or ADIFAB2 was the negative control. For each donor, two aliquots of serum were prepared: one "background" or "blank" sample of 1% serum and one "experimental" sample of 1% serum plus ADIFAB or ADIFAB2. The negative control, blank and experimental samples were measured at 22° C. or 37° C.

For each sample, multiple measurements of pairs of intensities were collected at about 432 nm and 505 nm, for ADIFAB and about 450 and 550 for ADIFAB2 and R values were determined after subtraction of the intensities of the blank sample. At least two separate measurements were done on different days for each serum sample and the mean values and standard deviations of $FFA_u$ concentrations were determined. To determine the probabilities of a difference between sets of measures, differences in means were evaluated using Student's t test, where a p value of less than 0.05 was considered significant.

The present disclosed method for detecting ischemia may further comprise the steps of taking measures to reduce the levels of ischemic markers. Also encompassed by the present disclosure is a method of determining prognosis of a patient following treatment for ischemia by detecting ischemia as disclosed herein and determining if the level of the ischemic marker is trending towards the level of the marker in the non-ischemic condition. The disclosed method also comprises the evaluation of the risks associated with elevated ischemic markers, either because the elevation of these markers reflects an underlying pathologic state and/or because the ischemic markers are themselves deleterious.

Example 1

[FFAu] are Elevated Before Troponin I in Patients Presenting to the Emergency Department (ED) with Different Forms of Myocardial Ischemia To determine the concentration of unbound free fatty acids [$FFA_u$] in patients suffering from a wide range of "natural" ischemic insults I measured $FFA_u$ levels in patients presenting to the emergency department (ED) of the Hennepin County Medical Center (Minneapolis, Minn.). Samples were drawn at admission and several times later from 29 patients. Each of these patients was diagnosed as having cardiac ischemia, primarily by ST segment changes. The diagnoses for these patients included: acute myocardial infarction (AMI), congestive heart failure (CHF), unstable angina, cardiac contusion, cardiac surgery, hypertension and cocaine induced ischemia. $FFA_u$ were significantly elevated in every patient diagnosed with cardiac ischemia, on average 20 times higher than normals (this study also included 48 "normal" patients whose average $FFA_u$ levels were 3 nM).

$FFA_u$ levels were elevated at the earliest draw (admission to the ED) in every patient, including the 9 AMI patients in this study (Table). In contrast, 7 of these 9 AMI patients showed no elevation of the cardiac marker Troponin I (TnI) at the time of admission. In these 7 patients TnI became elevated between 4 and 32 hours after admission. Furthermore, most of the non-AMI patients did not reveal elevated TnI levels, consistent with [$FFA_u$] being a marker of ischemia before necrosis.

Another noteworthy feature of these results is that in the absence of reperfusion therapy, $FFA_u$ levels remain elevated for long periods (up to days) after the initial ischemic event (Table). Thus $FFA_u$ respond rapidly to an ischemic event but return only slowly (presumably as the ischemia resolves) to base line, thereby providing a uniquely wide diagnostic window.

TABLE

Time course of TnI and
[FFA$_u$] in AMI[a]

| Patient | TIME (hours) | TnI (ng/ml) | [FFA$_u$] (nM) |
|---|---|---|---|
| 1 | 0 | 0.3 | 314 |
|   | 4 | 0.8 | 27 |
| 2 | 0 | 0.3 | 23 |
|   | 54 | 7.1 | 463 |
|   | 62 | 15.9 | 797 |
| 3 | 0 | 0.3 | 22 |
|   | 5 | 0.3 | 282 |
|   | 29 | 5.2 | 14 |
|   | 36 | 4.5 | 19 |
| 4 | 0 | 0.3 | 12 |
|   | 5 | 0.3 | 19 |
|   | 9 | 0.3 | 9 |
|   |   | 2.7 | 14 |
| 5 | 0 | 0.3 | 22 |
|   | 16 | 2.1 | 29 |
|   | 22 | 2.5 | 54 |
| 6 | 0 |   | 9 |
|   | 7 | 0.6 | 22 |
| 7 | 0 | 2. | 8 |
|   | 10 | 3.1 | 112 |
| 8 | 0 | 0.4 | 18 |
|   | 13 | 1 | 19 |
| 9 | 0 | 10.6 | 7 |
|   | 7 | 6.3 | 11 |
|   | 21 | 6.9 | 36 |
|   | 27 | 5.4 | 25 |
|   | 38 | 4.2 | 26 |
|   | 50 | 2.1 | 10 |

[a]Hennepin AMI patients. Time is hours from time of admission. Baseline TnI values were 0.3 ng/ml and normal [FFA$_u$] were 3 nM. Two or more serial measurements were done for each patient (separated by thick lines).

These results indicate the potential power of the FFA$_u$ assay; a serious ischemic event can be detected hours to days before current cardiac markers indicate disease, raising the possibility of earlier intervention and significant improvement in patient outcome.

Example 2

Results from the Thrombolysis in Myocardial Infarction II (TIMI-II) Trial Indicate High Sensitivity and Specificity for Detection of AMI using [FFAu] Measurements To obtain more detailed information about the FFA$_u$ response in acute myocardial infarction, I used blood specimens from the TIMI II trial (TIMI Study Group, New England Journal of Medicine (1989) vol. 320, page 618-625). These specimens have been maintained by the National Heart Lung Blood Institute and were made available for our investigations of FFA$_u$ levels in ischemia. Patients were enrolled in the TIMI II trial if they presented to an ED with chest pain within 4 hours of the initial symptoms and exhibited an ST segment elevation. Every patient was treated intravenously over 6 hours with either 100 mg (90.5% of the 3262 patients treated) or 150 mg (9.5% of the 3262 patients treated) t-PA starting within about 10 minutes of enrollment. Blood samples were drawn upon admission Oust before t-PA), 50 minutes after t-PA, and then 5 h and 8 h after start of t-PA treatment. A set of 4 such samples was stored at −70° C. for each of approximately 2,500 patients. For each patient, the TIMI investigators recorded about 825 clinical, physical and chemical observations.

Figure 2:
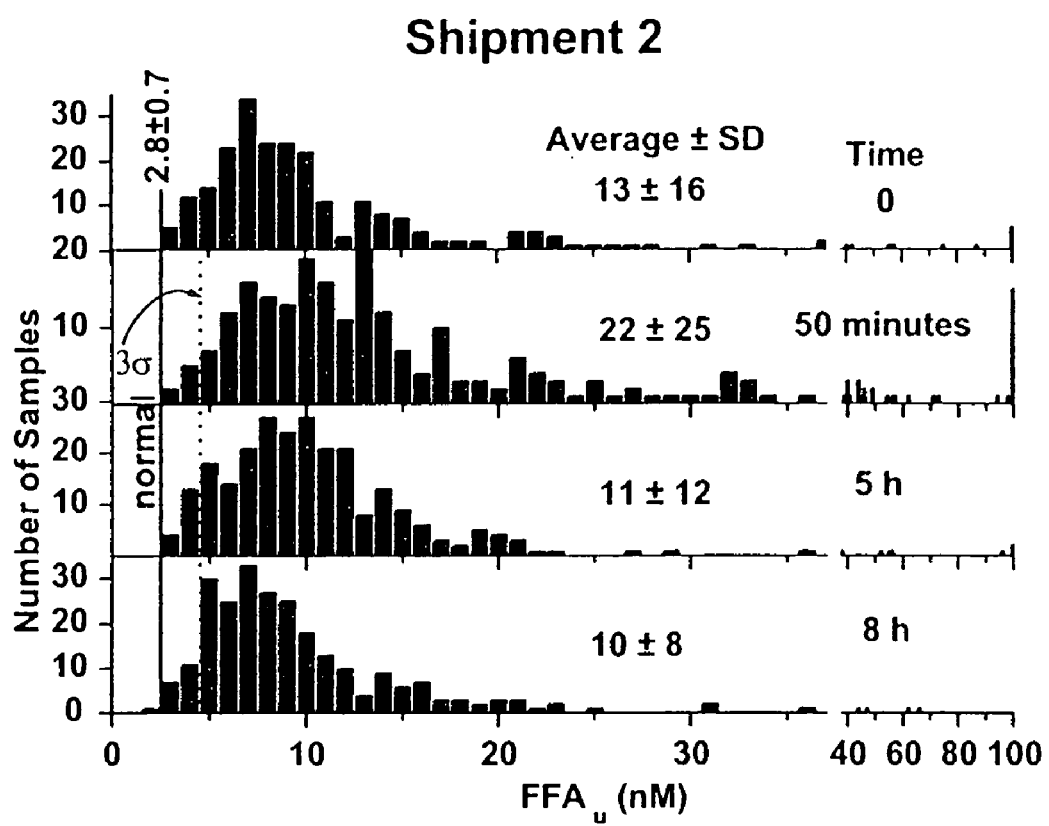
FIG. 2 shows $FFA_u$ results in the TIMI II study of patients with AMI. Histogram representation shows the results for the second set of 250 patients measured with ADIFAB2. The results are virtually identical to those in FIG. 1 for the first 250 patients.

Results for the first 500 patients provide important insights into the relationship between acute cardiac ischemia and FFA$_u$ levels. [Samples were received in individual shipments of 1000 samples (250 patients). FIGS. 1 and 2 show results for shipments 1 and 2, respectively.] (Kleinfeld, et al. (2002) J. Am. Coll. Cardiol. 39: 312A).

Upon admission the average FFA$_u$ (ADIFAB2) value was 13 nM, more than 14 standard deviations above the normal value (2.8±0.7 nM). This result demonstrates clearly that [FFA$_u$] are highly elevated, early in the ischemic event. Using a 5 nM cutoff, the predicted sensitivity for detection of AMI was 91% using FFA$_u$ at admission (using FFA$_u$ at admission and at 50 minutes increases sensitivity to >98%). The results show that >98% of the patients have FFA$_u$ levels >3 standard deviation above normal levels when the first two time points are included (>91% with only 1$^{st}$ time point).

Figure 3:
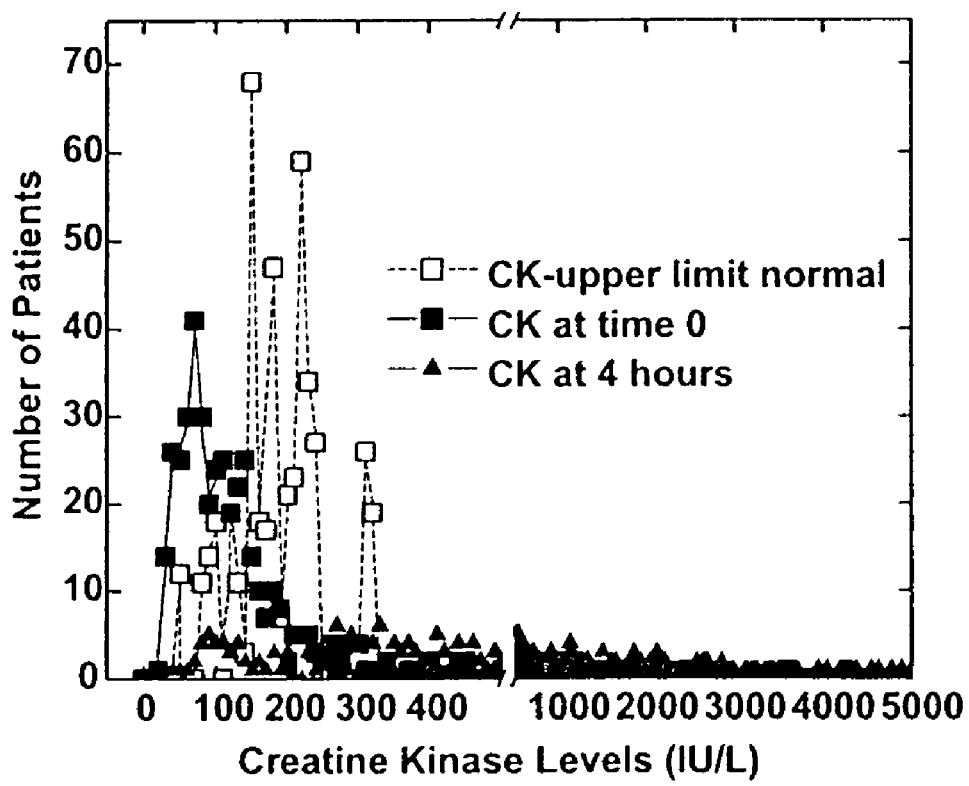
FIG. 3 shows creatine kinase (CK) levels in TIMI II patients at time 0 (admission time) (closed box, -■-) and at 4 hours (closed triangle, -▲-). Values were determined by the TIMI investigators for patients corresponding to shipments 1 and 2. The upper limit of normal was determined for each day's measurements and for each study site (open box, --□--).

At the same time, CK values at time 0 are generally less than the upper limit of normal (FIG. 3). Creatine kinase levels at admission were elevated in less than 19% of the patients and even in these patients the increases were modest, on average <50% above the upper limit of normal for the test. Not until 4 h post admission were creatine kinase levels elevated substantially in a majority of the patients.

At 50 minutes the average FFA$_u$ (22 nM) is substantially higher than the already elevated initial values. These samples were obtained about 50 minutes after administration of t-PA (FIGS. 1 and 2). The significantly higher average FFA$_u$ levels may reflect reperfusion effects and the ischemia mediated increases in [FFA$_u$] with increasing time. In any event, this time course appears to be changed abruptly by t-PA treatment because FFA$_u$ levels at 5 and 8 hours reveal significant decreases following reperfusion; the average value at 8 hours is significantly (p<0.05) lower than the FFA$_u$ level at time of admission. This biphasic response appears to be correlated with reperfusion because the AMI patients in the Hennepin study who did not receive reperfusion therapy reveal [FFA$_u$] that remained elevated for times greater than 24 h (data not shown). These findings, that FFA$_u$ may increase in response to reperfusion and then decrease within 5 h, indicate that FFA$_u$ levels might be used to evaluate the success of reperfusion therapy.

The [FFA$_u$] response of these patients appears to be an intrinsic and independent property of the pathology. FIGS. 1 and 2 reveal that measurements of the [FFA$_u$] distributions at each of the 4 different sample times, yield virtually identical parameters for the distributions of 2 different sets of 250 patients; samples in shipments 1 and 2 are for two sets of different patients. Moreover, almost all patients with confirmed MIs revealed FFA$_u$ (50 minutes)>[FFA$_u$] (admission), whereas for most of the approximately 3.3% of patients without confirmed MI, [FFA$_u$] (50 minutes)≦[FFA$_u$] (admission).

Example 3

High Levels of [FFAu] in TIMI-II Trial Samples at Time of Admission Correlate with Higher Mortality 3 Years Post Admission

Figure 4:
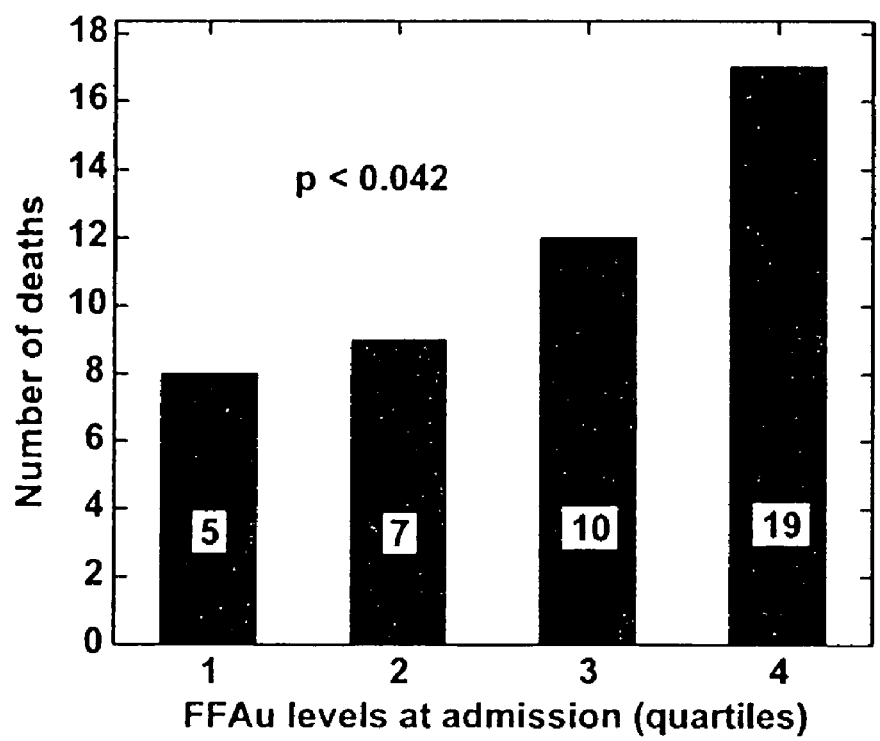
FIG. 4 shows mortality increases with [$FFA_u$] values at admission in TIMI II patients. About 400 of the 500 patients in this set had blood draws at time of admission. The levels of $FFA_u$ were sorted and the number of deaths in each quartile were determined. The results yield a positive correlation that increases by more than 2 fold from lowest to highest quartile ($p<0.042$). Median [$FFA_u$] for each quartile are shown in the bars.

[FFA$_u$] values at the time of admission are correlated with a more than 2-fold increase in mortality. [FFA$_u$] values for specimens drawn at time of admission (about 400 of the 500 patients) were sorted and partitioned into quartiles. The number of deaths, by any cause up to about 3 years after admission, were counted for each quartile. The primary (75%) cause of death was cardiovascular disease. The results show a more than 2 fold increase in death rate from lowest to highest quartile with a p value<0.025 (FIG. 4). In contrast, the cardiac marker, creatine kinase, was normal at the time of admission for most (>80%) of these patients (FIG. 3). Furthermore,

[FFA$_u$] values were not correlated with age, gender, race, weight, other disease, medications or systolic blood pressure on admission. These results indicate that in addition to their other diagnostic characteristics, FFA$_u$ levels measured at time of admission to the ED can be used to stratify patients according to their mortality risk (Kleinfeld, et al. (2002) J. Am. Coll. Cardiol. 39: 312A).

Example 4

High Levels of [FFAu] in TIMI-II Trial Samples at Time of Admission Correlate with Increased Rate of Severe Hemorrhage After t-PA Therapy

Figure 5:
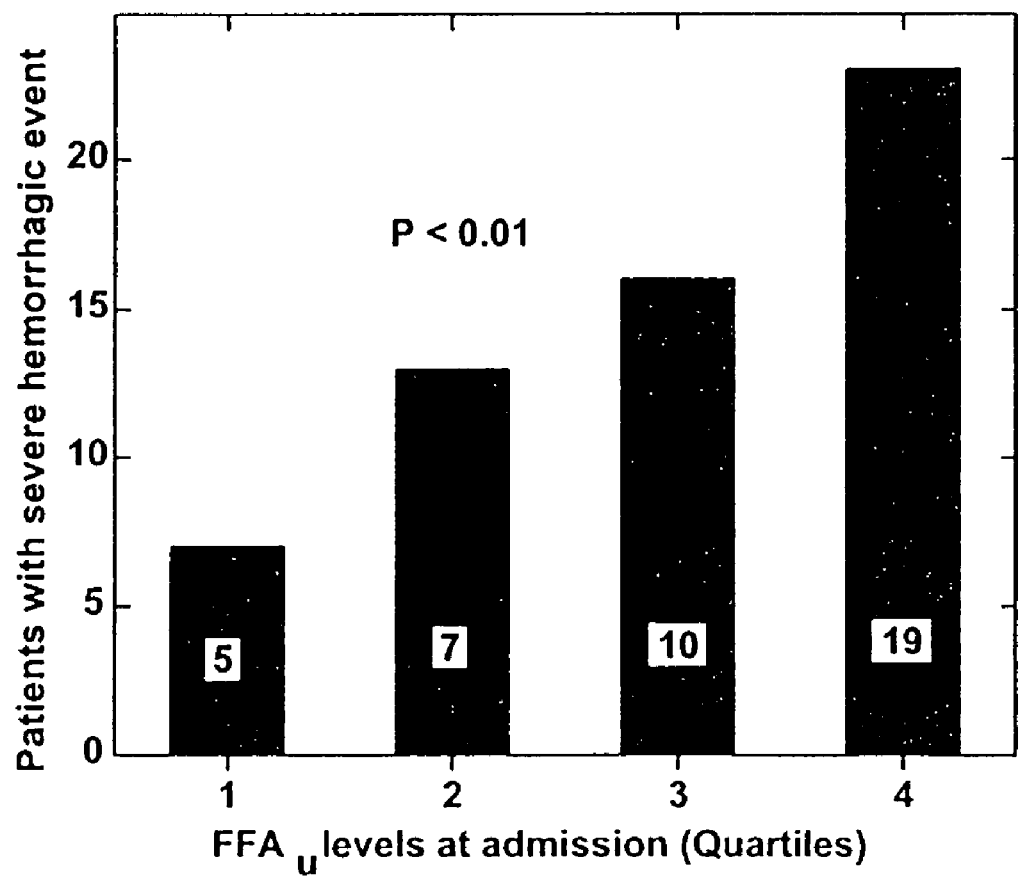
FIG. 5 shows the correlation between [$FFA_u$] at admission and severe hemorrhagic events in TIMI II patients. The number of severe hemorrhagic events per quartile of $FFA_u$ levels is shown. Numbers in the bars are the median [$FFA_u$] in nM. The results indicate a more than 3 fold increase in risk from lowest to highest quartile with a $p<0.01$.

[FFA$_u$] at admission also predict increased rates of severe hemorrhagic events after t-PA therapy. A similar analysis as for mortality (Example 3) was performed for severe hemorrhagic events. The number of patients that experienced severe hemorrhagic events was determined for each quartile (FIG. 5). The results reveal a more than 3 fold increase in the rate of severe hemorrhagic events from lowest to highest quartile of the distribution of [FFA$_u$] values at admission (before the start of t-PA administration) with p<0.01. One of the possibilities raised by these results is that rates of hemorrhage mediated by t-PA might be reduced if FFA$_u$ levels were lowered.

Although the results of FIGS. 4 and 5 do not indicate whether elevated FFA$_u$ levels directly and independently contribute to increased rates of death and hemorrhage, abundant in vitro work demonstrates that elevated FFA are potent perturbers of many cellular functions. In addition, clinical evidence for a direct role of FFA is strongly suggested by many studies pointing to their arrhythmogenic role and their potential role in cardiovascular disease. Results from our TIMI II trial also suggest that [FFA$_u$] are a strong independent factor of adverse outcomes. Thus, [FFA$_u$] do not simply reflect the demographics of this patient population; no correlation was observed with age, gender, race, or weight, for example. Moreover, the correlations of [FFA$_u$] at admission with mortality and hemorrhagic events, appear to be independent; although the mortality rate was higher for patients who experienced severe hemorrhagic events (22% vs 11% for all patients), only 15% of deaths were due to hemorrhage.

Example 5

Blood Levels of FFA in Ischemic Patients do not Originate from the Ischemic Tissue Cerebral and myocardial ischemia in humans result in increased plasma FFA levels by more than 7 fold above normal (Kleinfeld, et al. (1996) Amer. J. Cardiol. 78: 1350-1354; Kurien, et al. (1966) The Lancet 16: 122-127; Oliver, et al. (1994) The Lancet 343: 155-158). It is also well known that FFA accumulate within the cells of an ischemic tissue, at least for isolated organs (Bazan, et al. (1970) Biochim. Biophys Acta 218: 1-10; Van der Vusse, et al. (1997) Prostaglandins, Leukotrienes and Essential Fatty Acids 57: 85-93). However, this generation of FFA by ischemic tissue cannot account for the increases in plasma FFA observed in ischemia. This follows because the amount of FFA generated by the ischemic tissue, even under conditions of complete ischemia of the whole organ, is negligible compared to normal plasma FFA levels, let alone the more than 7 fold increases observed in ischemic patients. For example, under normal conditions plasma FFA turns over every 2 min. which at (normal) plasma total [FFA] of about 500 µM translates into about 0.2 g of FFA/min. The FFA produced in ischemic tissue derives from phospholipid (Bazan, et al. (1970) Biochim. Biophys Acta 218: 1-10; Goto, et al. (1988) Stroke 19: 728-735; Jones et al. (1989) Am. J. Pathol. 135: 541-556), which comprises less than 1% by (wet) weight of a typical (non-adipose) cell. Therefore, under ischemic conditions, where total FFA is 2 to 7 fold greater than the normal level, more than 20 g/min. of tissue would have to be used to maintain the observed levels of FFA. This is not compatible with life and indicates that increases in plasma FFA are derived from non-ischemic tissue.

In the specific example of complete cerebral ischemia (decapitation) the amount of total FFA that accumulates in rat brain over a period of 30 minutes is about 0.8 µmoles (Ikeda, et al. (1986) J. Neurochem. 47: 123-132). The total amount of plasma FFA in a 300 g rat is greater than 5 µmoles (>10 ml plasma of 500 µM FFA). In a rat model of reversible middle cerebral artery ischemia (a much less profound ischemic insult than decapitation), total plasma FFA increases about 2 fold and therefore an additional 5 µmoles of FFA is added to plasma every 2 minutes or about 75 µmoles in 30 minutes. Thus the 0.8 µmoles produced in 30 minutes of complete ischemia is negligible in comparison to the amount of FFA needed to raise plasma levels to those observed in ischemia. The most likely source of tissue with sufficient capacity to generate the large quantities of FFA observed in cerebral ischemia is adipose tissue. I have found that within minutes of cerebral ischemia increases are observed in plasma levels of TNF$_\alpha$, a potent activator of adipose lipolysis (Ryden, et al. (2002) J. Biol. Chem. 277:1085-1091) and that this TNF$_\alpha$ is well correlated with FFA$_u$ increases in plasma.

Example 6

[FFA$_u$] Correlates with Patient Outcome—EARLY RISK ASSESSMENT

Figure 6:
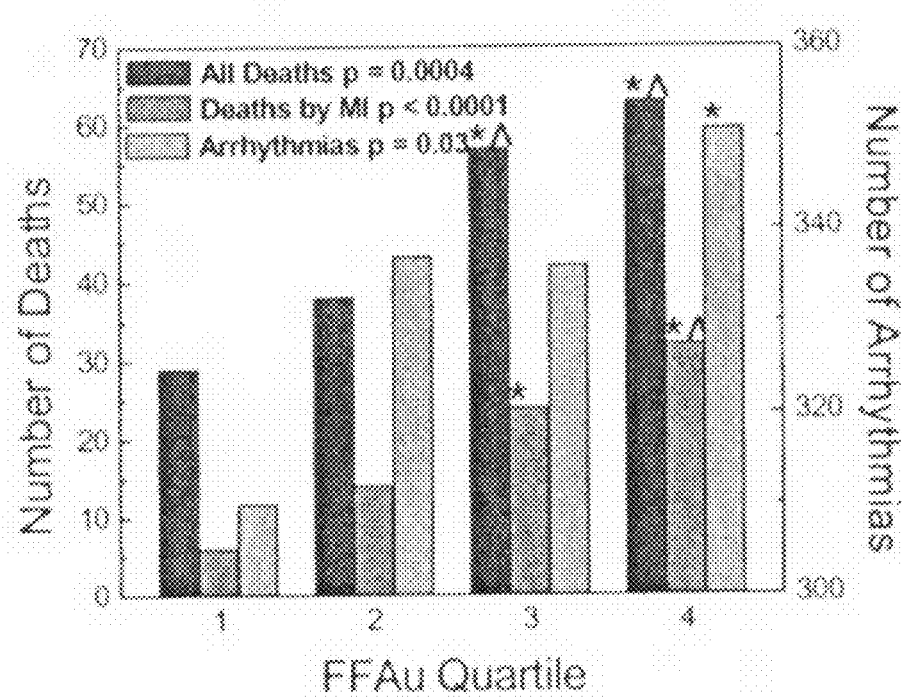
FIG. 6 shows correlation of death and arrhythmias with [FFAu]. Patient data was divided into quartiles with median [FFAu] of 1.9 (1), 3.2 (2), 4.9 (3), and 10.2 nM (4). The total number of deaths and deaths caused by MI increase 2 and 5-fold, respectively, from first to last quartile, and the number of patients who experienced arrhythmias increased 13%. The logisitic regression p-values are shown. Columns marked with * and ^ are significantly different from the first ($p<0.01$) and second ($p<0.05$) quartiles, respectively.

ADIFAB2 measurements of plasma samples from the TIMI II trial of patients with acute coronary symptoms, specifically with ST elevation myocardial infarctions (MI), indicate that total plasma [FFA$_u$] correlates with outcome for ACS patients. [FFA$_u$] values for specimens drawn from more than 1800 patients at time of admission (before heparin and t-PA therapy) were sorted and partitioned into quartiles. These samples were drawn within 4 hours (average of 2 hours) of symptom onset. Only 20% of these patients showed elevated creatine kinase levels, an indicator of cardiac cell death, at these early times. However, more than 90% of these patients had elevated FFA$_u$ levels. The number of deaths, by any cause up to about 3 years after admission, was counted for each quartile. The primary (73%) cause of death was cardiovascular disease. The results show a more than 2-fold increase in death rate from lowest to highest quartile (FIG. 6). Logistic regression yields a p value of 0.0004, indicating that the difference between quartiles is highly significant. An even stronger correlation is seen between [FFA$_u$] and death caused by MI. In this case, the death rate increased more than 5-fold from the first to fourth quartile (p<0.0001). A somewhat weaker, but significant (p=0.03), correlation was also seen between [FFA$_u$] and frequency of arrhythmias. The number of patients with arrhythmias increased by 13% from the first to fourth FFA$_u$ quartile. In addition, the number of severe hemorrhagic events increases by 46% from the first (50 events) to the fourth (73 events) [FFA$_u$] quartile (data not shown).

On the other hand, no statistically significant correlation of [FFA$_u$] with age, gender, race, body mass index, and systolic blood pressure on admission was found (data not shown).

These results are the first to indicate any marker that can stratify ACS patients for risk of death and other deleterious outcomes at such early times in the course of the disease. This indicates that $FFA_u$ levels measured at time of admission can help predict patient outcome and may lead to early interventions to improve outcomes. $FFA_u$ levels measured at the earliest time such as onset of symptoms such as difficulty breathing, chest pain, sudden weakness, sweating, nausea, vomiting, breathlessness, loss of consciousness, palpitations or confusion or admission to a hospital emergency room, predict patient outcome.

In fact, the observed correlations of [FFAu] with the occurrence of arrhythmias and death in the TIMI II study suggest that the elevations in FFAu have a negative impact on outcome. Thus a therapeutic intervention designed to reduce $FFA_u$ levels, for example GIK, at very early times might significantly improve outcome, especially in patients with the highest $FFA_u$ levels.

Figure 7:
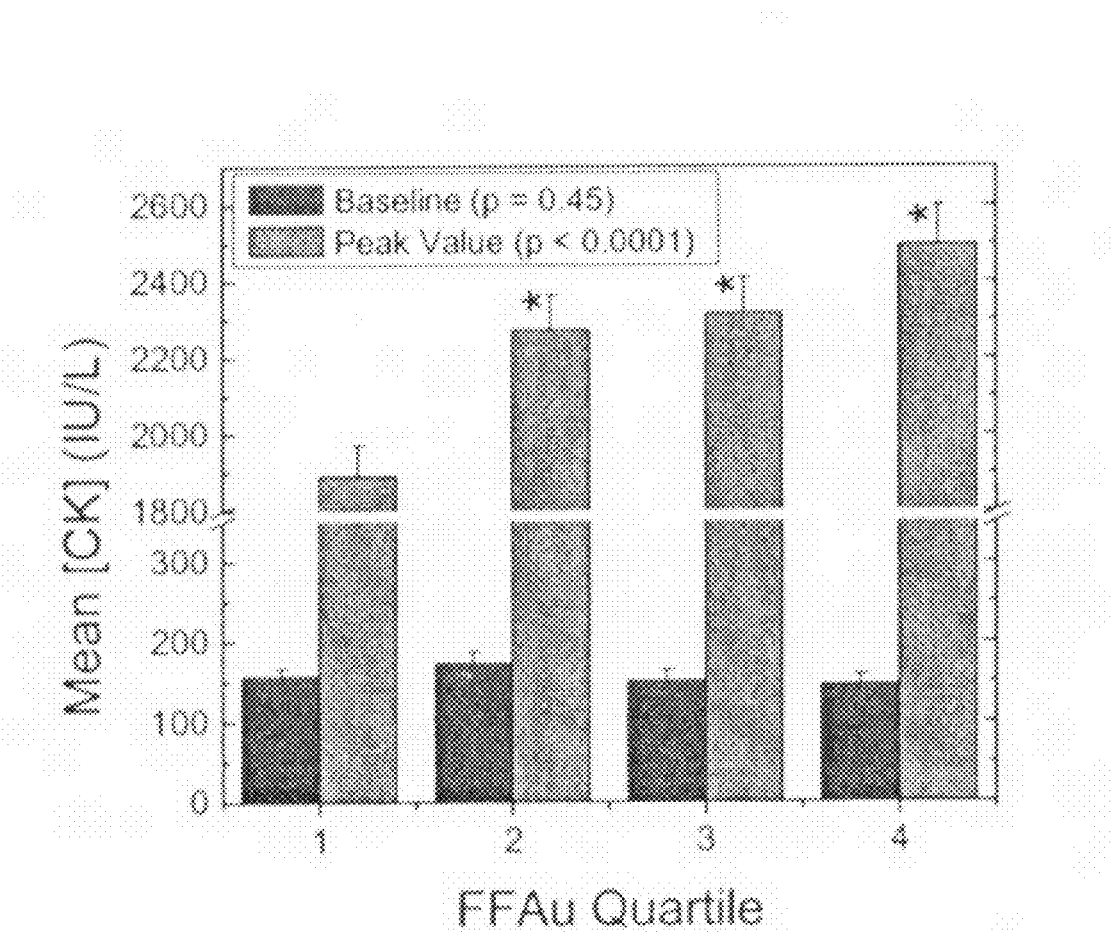
FIG. 7 shows [FFAu] correlates with peak CK but not baseline CK levels. Patient data was divided into quartiles with median [FFAu] of 1.9 (1), 3.2 (2), 4.9 (3), and 10.2 nM (4). The mean (+ standard error) baseline and peak CK levels are shown for each quartile. No difference between quartiles is observed for baseline CK. Mean peak CK levels for quartiles 2, 3, and 4 are significantly different from the mean for quartile 1 with $p=0.02$, $p=0.006$, and $p<0.0001$ by Tukey's HSD post hoc test.

These results indicate that the $FFA_u$ response in ACS is correlated with the underlying pathology, and that $[FFA_u]$ reflect the severity of disease. To determine whether $[FFA_u]$ reflect the degree of disease, $[FFA_u]$ were correlated with creatine kinase (CK) (TIMI II). The results indicate that $FFA_u$ levels at presentation are not correlated with CK levels at presentation but are positively correlated with peak (within 24 hrs of presentation) CK levels. The first draw samples from TIMI II were split into $FFA_u$ quartiles and the average CK baseline and peak values were calculated for each quartile (FIG. 7). Analysis of variance reveals no significant (p=0.45) difference between the mean baseline CK levels but a highly significant (p<0.0001) difference between the mean peak CK levels, for which a 32% increase was observed from the first to the fourth $FFA_u$ quartile. The lack of a correlation between $[FFA_u]$ and CK levels at presentation likely results from the poor sensitivity of CK at early times; only 20% of the TIMI II patients had CK elevations at presentation. These results provide further evidence that plasma $[FFA_u]$ is an early marker of cardiac ischemia that can be used to predict risk of MI at presentation. Furthermore, the association of $[FFA_u]$ with disease severity is consistent with the findings that $[FFA_u]$ at presentation are a predictor of mortality (FIG. 6).

Example 7

Using [FFAu] to Monitor Therapy

Figure 8:
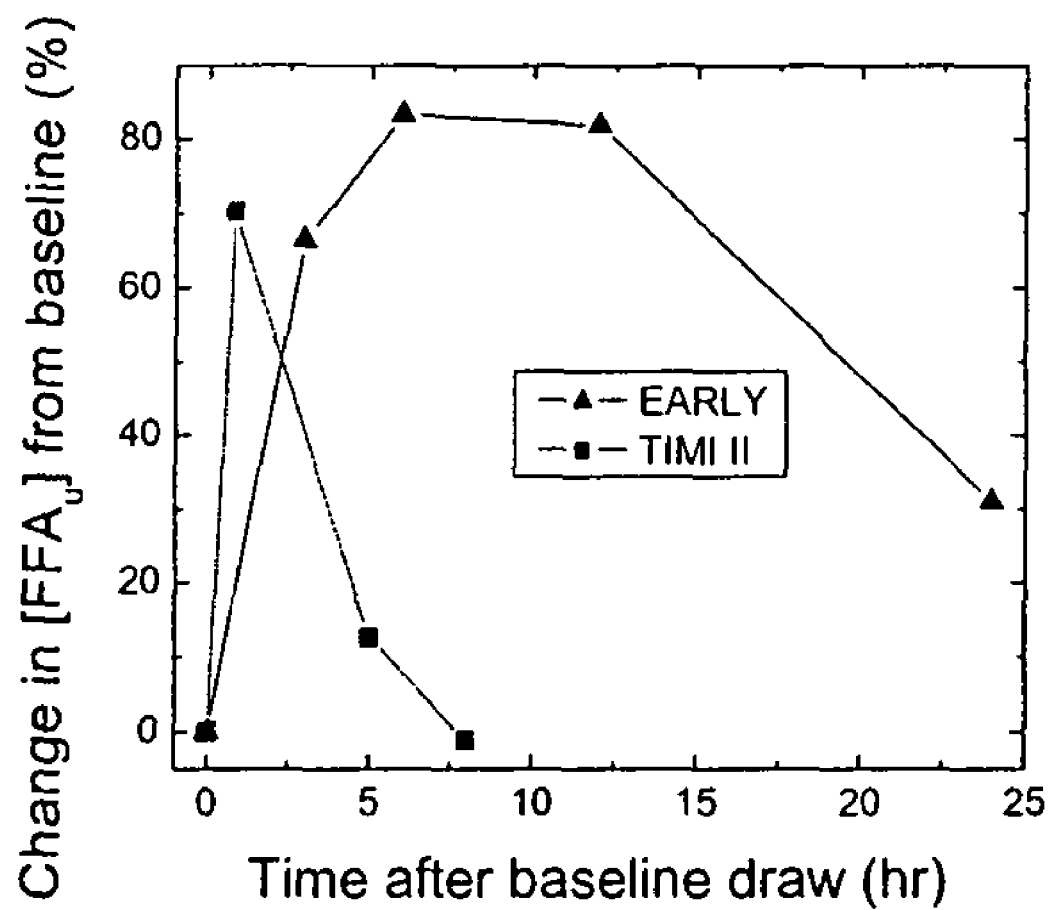
FIG. 8 shows different [FFAu] time courses for EARLY and TIMI II patients. Four and five serial blood draws were taken from the TIMI II (squares) and EARLY (triangles) patients, respectively. The change in [FFAu], as measured with ADIFAB2, was determined relative to the baseline value. TMI II patients displayed a much faster time course.

Serial blood draws were taken from patients enrolled in both the TIMI II (STEMI) and EARLY (patients with unstable angina and non-STEMI) studies of ACS. ADIFAB2 measurements for both studies indicate that the median $[FFA_u]$ peaks after the first draw and approaches baseline at later times (FIG. 8). However, the time scales of the changes in plasma $[FFA_u]$ are dramatically different between these two populations. The $[FFA_u]$ both rises and returns to baseline more rapidly for TIMI II patients than for EARLY patients. I propose that the difference between the time courses originates from the different therapies administered in the two studies. All patients in TIMI II were treated with heparin and tissue plasminogen activator (tPA) after the first time point, whereas EARLY patients were given aspirin, heparin, and eptifibatide (or placebo), after the first time point. This suggests that the large $FFA_u$ increase at TIMI draw 2 (~50 minutes after the start of tPA and heparin) is due to washout of lipolytic agents from the occluded artery after tPA-mediated patency and/or direct effects of reperfusion (injury). The ensuing rapid (relative to EARLY) return to baseline $[FFA_u]$ is likely indicative of the efficacy of reperfusion therapy and show that $[FFA_u]$ measurements offer a means to monitor reperfusion therapy. The EARLY patients, having less severe indications of ACS, were provided a less aggressive therapy and, therefore, did not experience the same rapid reperfusion as TIMI II patients, as indicated by the $[FFA_u]$ time course. In fact, the primary finding of the EARLY trial was that eptifibatide did not affect infarct size in NSTEMI patients (Roe M T, et al. *Am Heart J* 146: 993-998, 2003).

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A method of identifying patients at risk of mortality at three years after an ischemic event, at risk for hemorrhage after receiving reperfusion therapy or long-term risk of mortality or arrhythmia in a non-acute patient comprising the steps of:
    measuring the level of an ischemic marker in a body fluid sample from said patient before anti-ischemic treatment, wherein the ischemic marker is unbound free fatty acid;
    comparing the measured level of the ischemic marker from the patient to a threshold level of the ischemic marker, wherein a threshold level of unbound free fatty acid of 1.5 to 2.5 nM signifies low risk, a threshold level of unbound free fatty acid of 2.5 to 4.0 nM signifies low to medium risk, a threshold level of 4.0 to 7.5 nM unbound free fatty acid signifies medium to high risk and a threshold level of unbound free fatty acid greater than 7.5 nM signifies highest risk, wherein said threshold level is determined from measuring the ischemic marker in body fluid of an ischemic population; and
    correlating the measured level of the ischemic marker from the patient with the threshold level, thereby identifying patients at risk of mortality at three years after an ischemic event, at risk for hemorrhage after receiving reperfusion therapy or long-term risk of mortality or arrhythmia in a non-acute patient.

2. The method of claim 1, wherein the anti-ischemia treatment is selected from reperfusion therapy, antithrombolytic therapy, angiogenic therapy, surgery and combinations thereof.

3. The method of claim 2, wherein the treatment is reperfusion therapy and wherein said reperfusion therapy comprises angioplasty.

4. The method of claim 2, wherein the treatment is reperfusion therapy and wherein said reperfusion therapy comprises administration of a thrombolytic agent.

5. The method of claim 1, wherein the level of unbound free fatty acid is determined in plasma or serum.

6. The method of claim 1, wherein the level of unbound free fatty acid is determined by binding to acrylodan labeled intestinal fatty acid binding protein with a substitution of Ala for Leu at position 72 (ADIFAB2).

7. The method of claim 6, wherein the binding is carried out at a temperature of 20-24° C.

8. The method of claim 1, wherein the risk of mortality is correlated with increased levels of unbound free fatty acid due to cardiovascular disease.

9. The method of claim 8, wherein the cardiovascular disease is myocardial infarction.

* * * * *

UNITED STATES PATENT AND TRADEMARK OFFICE
CERTIFICATE OF CORRECTION

| | |
|---|---|
| PATENT NO. | : 7,879,558 B2 |
| APPLICATION NO. | : 11/841480 |
| DATED | : February 1, 2011 |
| INVENTOR(S) | : Kleinfeld |

It is certified that error appears in the above-identified patent and that said Letters Patent is hereby corrected as shown below:

Page 2, Column 1, Other Publications, Line 18, "Samanta, et a." should be changed to --Samanta, et al.--

Column 7, Line 61, "logisitic regression" should be changed to --logistic regression--

Column 10, Line 27, "the label is acryolodan." should be changed to --the label is acrylodan.--

Column 13, Line 60, "Oust before t-PA)," should be changed to --(just before t-PA),--

Signed and Sealed this
Sixteenth Day of August, 2011

David J. Kappos
*Director of the United States Patent and Trademark Office*

UNITED STATES PATENT AND TRADEMARK OFFICE
CERTIFICATE OF CORRECTION

PATENT NO.         : 7,879,558 B2                                     Page 1 of 1
APPLICATION NO.    : 11/841480
DATED              : February 1, 2011
INVENTOR(S)        : Alan Kleinfeld It is certified that error appears in the above-identified patent and that said Letters Patent is hereby corrected as shown below:

Column 18, Line 17, "of mortality at" should be changed to --of mortality within--

Column 18, Line 38, "of mortality at" should be changed to --of mortality within--

Signed and Sealed this
Twenty-fifth Day of September, 2012

David J. Kappos
*Director of the United States Patent and Trademark Office*